United States Patent
Kang et al.

(10) Patent No.: US 10,064,812 B2
(45) Date of Patent: Sep. 4, 2018

(54) ANTI-AGING COMPOSITION FOR VITALIZATION OF RETINOIC ACID RECEPTOR THAT CONTAINS MIXED EXTRACT OF CHINESE MATRIMONY VINE AND PINE NEEDLES AS EFFECTIVE COMPONENT

(71) Applicant: Amorepacific Corporation, Seoul (KR)

(72) Inventors: Young Gyu Kang, Yongin-si (KR); Jun Seong Park, Yongin-si (KR); Jee Yeun Kim, Yongin-si (KR); Yong Joo Na, Yongin-si (KR); Nok Hyun Park, Yongin-si (KR); Myeong Hun Yeom, Yongin-si (KR); Jun Cheol Cho, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 641 days.

(21) Appl. No.: 14/830,005

(22) Filed: Aug. 19, 2015

(65) Prior Publication Data

US 2015/0352037 A1   Dec. 10, 2015

Related U.S. Application Data

(63) Continuation of application No. 14/349,839, filed as application No. PCT/KR2012/008141 on Oct. 9, 2012.

(30) Foreign Application Priority Data

Oct. 11, 2011   (KR) ........................ 10-2011-0103448

(51) Int. Cl.
| | | |
|---|---|---|
| A61K 36/00 | (2006.01) | |
| A61K 8/97 | (2017.01) | |
| A61Q 19/08 | (2006.01) | |

(52) U.S. Cl.
CPC ................ *A61K 8/97* (2013.01); *A61Q 19/08* (2013.01); *A61K 2800/5922* (2013.01); *A61K 2800/78* (2013.01)

(58) Field of Classification Search
None
See application file for complete search history.

(56) References Cited

U.S. PATENT DOCUMENTS

2011/0311662 A1   12/2011   Ha et al.
2013/0251827 A1   9/2013   Ha et al.

FOREIGN PATENT DOCUMENTS

WO   2010/098596 A2   9/2010

OTHER PUBLICATIONS

Jeong et al; "Effect of extracts from pine needle against oxidative DNA damage and apoptosis induced by hydroxyl radical via antioxidant activity"; Food and Chemical Toxicology 47; 2009; pp. 2135-2141.
Li et al; "Antioxidant properties in vitro and total phenolic contents in methanol extracts from medicinal plants"; ScienceDirect; LWT 41; 2008; pp. 385-390.
Raskin et al; "Can an Apple a Day Keep the Doctor Away?"; Current Pharmaceutical Design; 2004; 10; pp. 3419-3429.
Hsu et al; "Difference in the effects of radioprotection between aerial and root parts of Lycium chinese"; Journal of Ethnopharmacology 64; 1999; pp. 101-108.
Qian et al; "The efficiency of flavonoids in polar extracts of Lycium chinese Mill fruits as free radical scavenger"; Food Chemistry 87; 2004; pp. 283-288.
Masaki; Role of antioxidants in the skin: Anti-aging effects; Journal of Dermatological Science 58; 2010; pp. 85-90.
Revilla; "Comparison of Several Procedures Used for the Extraction of Anthocyanins from Red Grapes"; J. Agric. Food Chem. 1998; 46; pp. 4592-4597.

*Primary Examiner* — Christopher R Tate
*Assistant Examiner* — Russell G Fiebig
(74) *Attorney, Agent, or Firm* — Sughrue Mion, PLLC

(57) ABSTRACT

Provided are an anti-aging composition that contains a mixed extract of Chinese matrimony vine and pine needles as an effective component and a method of inhibiting aging of skin. The composition is for an external application to the skin, wherein a mixed extract of Chinese matrimony vine and pine needles, which are the natural ingredients, is contained such that excellent anti-aging or wrinkle improvement effects to the skin can be obtained through the vitalization of a retinoic acid derivative.

10 Claims, No Drawings

ANTI-AGING COMPOSITION FOR VITALIZATION OF RETINOIC ACID RECEPTOR THAT CONTAINS MIXED EXTRACT OF CHINESE MATRIMONY VINE AND PINE NEEDLES AS EFFECTIVE COMPONENT

CROSS-REFERENCE TO RELATED APPLICATIONS

This is a Continuation of U.S. application Ser. No. 14/349,839 filed Apr. 4, 2014 which is a National Stage Entry of PCT International Application No. PCT/KR2012/008141 filed Oct. 9, 2012, which claims benefit of Korean Patent Application No. 10-2011-0103448 filed Oct. 11, 2011 of which disclosures are incorporated herein by reference in their entirety.

TECHNICAL FIELD

The present invention relates to an anti-aging composition containing a mixture of *Lycium chinense* fruit extract and pine needle extract as an active ingredient. More particularly, the present invention relates to an anti-aging composition containing, as an active ingredient, a mixture of *Lycium chinense* fruit extract and pine needle extract that exhibits an anti-aging effect by activating retinoic acid receptor.

BACKGROUND ART

The phenomena of aging are deepened as human beings grow older. Particularly, in the case of the skin, the change is remarkable. The main phenomena of skin aging are an increase in wrinkles, skin thickening, inelasticity, dryness, roughness, spot, etc., which are believed to be caused by skin exposure to sunlight over a long period of time. Such phenomena by sunlight are called photo-aging and are caused by the changes in epidermal and dermal tissues due to the sunlight. It has been reported that photo-aging of the skin may be alleviated when a cream containing tretinoin (all-trans-retinoic acid), retinol and derivatives thereof, AHAs, etc. are applied to the skin. However, because tretinoin is fat-soluble, it has low absorbability. Also, it is unstable in the living body, is irritant to the skin, and may cause some side-effects such as skin dryness, wounds, scraping, etc. during the latent period. Therefore, there are many problems in using tretinoin as a main component for medicines and cosmetics (U.S. Pat. No. 4,677,120). On the other hand, retinol that is vitamin A can hardly be used because it is unstable to light, oxygen, heat, lipid peroxides, or water. Therefore, in order to use retinol, additional cost should be paid for stabilizing it by anti-oxidants such as BHT, di-α-tocopherol, BHA, ascorbic acid, tocopheryl linolate, etc., or by adopting some means such as liposomes or capsules for intercepting from outside effects (U.S. Pat. Nos. 6,221,927 and 5,744,148).

Thus, there have been active studies on materials that prevent or alleviate skin aging by activating retinoic acid receptor (RAR) and also have no side effects on the skin and are safe to the skin. The present invention is a result of such studies and is based on the finding that a skin external composition containing a mixture of extracts of *Lycium chinense* fruits and pine needles that are natural materials has an excellent effect on the prevention of skin aging.

Up to now, this effect of a mixture of extracts of *Lycium chinense* fruits and pine needles has not yet been reported.

The *Lycium chinense* fruit that is the fruit of *Lycium chinense* Miller is pointed at one end and pyramidal in shape, and the pericarp thereof is red or dark red in color. The outer surface thereof is crumpled, and it contains yellowish white seeds. The seeds have a flat oval shape and a diameter of about 2 mm. The *Lycium chinense* fruit has little or no odor, and the taste is somewhat sweet and astringent. The major pharmacological effects thereof include liver cell protection, blood pressure lowering, immune function enhancement and regulation, anti-aging, anti arteriosclerosis, female hormone-like effects, anti-tumor, blood formation stimulation, etc.

Pine needles are the needles and buds of a pine tree (*Pinus sylvestris*). Fresh pine needles contain large amounts of ascorbic acid and vitamin A, B and K, bitter taste compounds, flavonoids, anthocyans, 7-12% rosin, about 5% tannin, carbohydrates, essential oil (0.13-1.3 wt % in needles, 0.36% in buds, and 0.2-0.9% in one-year-old twigs), etc. In addition, the whole pine tree include components that discharge waste products (alcohol, ester, etc.) and promote metabolism, phenolic compounds, kinin, turpentine, vitamins A and C, chlorophyll-based substances, glycokinin, abietic acid, etc., and is rich in iron. It was found that red pine needles contain 24 kinds of amino acids and also 19 kinds of amino acids composed of protein. Pine needles are the source of vitamin C. Pine needles are deep green in color, and thus rich in carotene. The pharmacological effects of pine needles may be the general effects of terpene, phenolic compounds, tannin and the like, and the nutritional effects may be the effects of various nutrients and inorganic components, including fats, proteins, carbohydrates, vitamins and minerals. It was found that pine needles are rich in various mineral components, including chlorophyll vitamin A, vitamin C, vitamin P, proteins, fats, phosphorus, iron, enzymes, and essential oil, and thus exhibit an excellent effect on the removal of cholesterol. Also, pine needles contain 0.00355% calcium, 0.043% potassium, 0.2% maleic acid, 0.3198% glycine, 0.3467% serine, 0.00376% vitamin P (rutin), 0.0015% vitamin A, and 0.1301% vitamin C. In addition, pine needles are useful for the prevention of hypertension, palsy, diabetes, dementia and aging and have anticancer effects. Additionally, pine needles are beneficial for the liver and stomach, are useful for the alleviation of constipation, anemia, chronic alcoholism and hangover, nicotine removal, skin cosmetic, constitution improvement, dietaries, male stamina enhancement, and clear the head when the head feels heavy and the eyesight dims due to various stresses and excessive smoking and drinking, and thus are beneficial for students. 100 g of pine trees contain water (42.9%), crude protein (0.07%), glucose (30.6%), and natural nutrients such as minerals (K, Ca, Fe, Mg, and P) and vitamins. With respect to food nutritional components and functions, chlorophyll has hematopoietic activity (increase in hemoglobin), increases the growth of granulation tissue (regeneration of damaged tissue), activates brain cells, reduces cholesterol, and promotes the growth of tissues and cells.

DISCLOSURE

Technical Problem

The present inventors have performed various repeated experiments to provide a composition having a skin aging-preventing effect using natural materials that have no side effects on the skin and are safe. As a result, the present inventors have found that, when a mixture of extracts of

*Lycium chinense* fruits and pine needles that are natural materials is used as a skin external composition, it exhibits an excellent effect on the prevention of skin aging, thereby completing the present invention.

Therefore, it is an object of the present invention to provide a skin external composition containing, as an active ingredient, a mixture of *Lycium chinense* fruit extract and pine needle extract, which has an excellent anti-aging effect.

Technical Solution

To achieve the above object, the present invention provide a skin external composition for anti-aging, which contains a mixture of *Lycium chinense* fruit extract and pine needle extract as an active ingredient.

Advantageous Effects

The composition according to the present invention contains a mixture of *Lycium chinense* fruit extract and pine needle extract, which activates retinoic acid receptor and inhibits the expression of collagenase to thereby exhibit wrinkle-reducing effects and anti-aging effects. In addition, the composition containing the mixture of the extracts has less side effects and is safe, and thus can be used in various applications, including cosmetic or drug products.

Best Mode

The present invention relates to a composition containing a mixture of *Lycium chinense* fruit extract and pine needle extract as an active ingredient. More specifically, the present invention relates to an anti-aging composition containing, as an active ingredient, a mixture of *Lycium chinense* fruit extract and pine needle extract that exhibits an anti-aging effect by activating retinoic acid receptor.

A method for preparing the mixture of *Lycium chinense* fruit extract and pine needle extract are not specifically limited and may be performed by any conventional method known in the art. For example, the *Lycium chinense* fruit extract can be obtained by washing, drying and finely powdering *Lycium chinense* fruits, extracting the powder with water or an organic solvent, filtering the extract through filter cloth, aging the filtrate, filtering the aged filtrate, extracting the resulting filtrate using a separatory funnel, concentrating the separated extract under reduced pressure, and drying the concentrate. The pine needle extract can also be obtained in the same manner, and the obtained extracts are mixed with each other to obtain a mixture of the extracts. Herein, the *Lycium chinense* fruit extract and the pine needle extract are preferably mixed with each other at a ratio of 1:1.

An organic solvent that is used in the present invention may be selected from among ethanol, methanol, butanol, ether, ethyl acetate, chloroform, and a mixture of one or more of these organic solvents with water. Preferably, 70% ethanol is used in the present invention. The extraction temperature is preferably 25-30° C., and the extraction time is preferably 24-26 hours. If the extraction temperature and the extraction time are out of the above-specified ranges, the extraction efficiency can decrease or a change in the components of the extract can occur. In addition, the aging temperature of the filtrate is preferably 4-15° C., and the aging time is preferably 5-7 days. If the aging temperature and the aging time are out of the above-specified ranges, a change in the components of the filtrate can occur.

The contents of the *Lycium chinense* fruit extract and the pine needle extract in the composition of the present invention are not specifically limited. Specifically, the content of the *Lycium chinense* fruit extract in the mixture of *Lycium chinense* fruit extract and the pine needle extract of the composition according to the present invention may be 40-60 wt %, and preferably 45-55 wt %, based on the total weight of the mixture. If the content of the *Lycium chinense* fruit extract is less than 40 wt %, the skin anti-aging effect of the composition will be insignificant, and if it is more than 60 wt %, the increase in the content of the extract will not lead to a significant in the effect. In addition, the content of the pine needle extract in the mixture of *Lycium chinense* fruit extract and the pine needle extract of the composition according to the present invention may be 40-60 wt %, and preferably 45-55 wt %, based on the total weight of the mixture. If the content of the pine needle extract is less than 40 wt %, the skin anti-aging effect of the composition will be insignificant, and if it is more than 60 wt %, the increase in the content of the extract will not lead to a significant in the effect.

The composition according to the present invention contains, as an active ingredient, a mixture of *Lycium chinense* fruit extract and pine needle extract that exhibits an anti-aging effect. More specifically, the mixture of *Lycium chinense* fruit extract and pine needle extract exhibits a skin aging inhibitory or wrinkle reducing effect by activating retinoic acid receptor, inhibiting the expression of collagenase to promote the production of collagenase, and alleviating the reduction in collagen caused by aging of human skin.

The composition of the present invention may be a skin external composition, particularly, an anti-aging composition or a wrinkle-reducing composition.

When the skin external composition according to the present invention is formulated as a cosmetic composition, it may be formulated in the form of skin lotion, milk lotion, massage cream, nourishing cream, moisturizing cream, hand cream, foundation, essence, nourishing essence, cream, soap, cleansing foam, cleansing lotion, cleansing cream, body lotion, body cream or pack, but the formulation of the composition is specifically limited. In addition, the composition according to the present invention may be a pharmaceutical composition having a formulation such as a suspension, ointment, lotion or spray formulation. Other components in each formulation can be suitably selected without difficulty by those skilled in the art depending on the kind and intended use of formulation.

Mode for Invention

Hereinafter, the present invention will be described in further detail with reference to examples and test examples. It is to be understood, however, that these examples and test examples are for illustrative purposes only and are not intended to limit the scope of the present invention.

EXAMPLE 1

Preparation of *Lycium chinense* Fruit Extract

*Lycium chinense* fruits were washed with purified water, washed and finely powdered. 200 g of the *Lycium chinense* fruit powder was added to 1 liter of an aqueous solution of 70% ethanol and extracted by heating for 12 hours in an extractor equipped with a cooling condenser. The extract was filtered through 300-mesh filter cloth, and the filtrate was allowed to stand at 4-15° C. for 7 days, and then filtered through Whatman No. 2 filter paper.

The filtered extract was placed in a 3-liter separatory funnel, and 1 liter of ethyl acetate was added thereto. Then, the solution was mixed well by shaking. After the solution was completely separated into two layers, the upper layer (ethyl acetate layer) was collected. The lower layer (aqueous layer) was extracted twice more using a separatory funnel.

The separated upper layers were combined with each other and concentrated under reduced pressure at 50° C. using a distillation apparatus equipped with a cooling condenser, and the concentrate was dried, thereby obtaining 38.5 g (dry weight) of a *Lycium chinense* fruit extract.

EXAMPLE 2

Preparation of Pine Needle Extract

Pine needles were washed with purified water, washed and finely powdered. 200 g of the pine needle powder was added to 1 liter of an aqueous solution of 70% ethanol and extracted by heating for 12 hours in an extractor equipped with a cooling condenser. The extract was filtered through 300-mesh filter cloth, and the filtrate was allowed to stand at 4-15° C. for 7 days, and then filtered through Whatman No. 2 filter paper.

The filtered extract was placed in a 3-liter separatory funnel, and 1 liter of ethyl acetate was added thereto. Then, the solution was mixed well by shaking. After the solution was completely separated into two layers, the upper layer (ethyl acetate layer) was collected. The lower layer (aqueous layer) was extracted twice more using a separatory funnel.

The separated upper layers were combined with each other and concentrated under reduced pressure at 50° C. using a distillation apparatus equipped with a cooling condenser, and the concentrate was dried, thereby obtaining 24.9 g (dry weight) of a pine needle extract.

TEST EXAMPLE 1

Wrinkle-reducing Effect

Using the *Lycium chinense* fruit extract obtained in Example 1, the pine tree extract obtained in Example 2, and a 1:1 (w/w) mixture (Example 3) of a *Lycium chinense* fruit extract obtained by extracting 100 g of *Lycium chinense* fruits according to the method of Example 1 and a pine needle extract obtained by extracting 100 g of pine needles according to the method of Example 2, their effects on the inhibition of collagenase expression (collagenase production) were measured in the following manner. As a positive control, retinoic acid known to inhibit collagenase expression was used.

First, human fibroblasts were added to a 96-well microtiter plate containing DMEM (Dulbecco's Modified Eagle's Media) containing 2.5% fetal bovine serum at a density of 5,000 cells/well and were cultured to a confluence of 90%. Then, the cells were cultured in serum-free DMEM medium for 24 hours and treated with each of 100 μg/ml of the extract of Example 1, 100 μg/ml of the extract of Example 2, a mixed extract (Example 3) obtained by mixing 100 μg/ml of the extract of Example 1 with 100 μg/ml of the extract of Example 2, and 1 μM of retinoic acid, which were test materials dissolved in serum-free DMEM medium, for 24 hours. Then, the cell cultures were harvested.

Next, the degree of collagenase production in each of the harvested cell cultures was measured using a collagenase measurement device (Amersham Phamasia, USA). Specifically, each of the harvested cell cultures was placed added to a 96-well plate having primary collagenase antibody applied uniformly thereto and were subjected to an antigen-antibody reaction in an incubator for 3 hours. After 3 hours, chromophore-conjugated secondary collagen antibody was added to the 96-well plate and allowed to react for 15 minutes. After minutes, a substance that induces color development was added to the 96-well plate, and color development was induced at room temperature for 15 minutes. When 1 M sulfuric acid was added to the 96-well plate to stop the color development reaction, the reaction solution had a yellow color, and the intensity of the yellow color varied depending on the degree of progression of the reaction.

The absorbance of the 96-well plate having a yellow color was measured at 405 nm using an absorbance spectrometer, and the expression of collagenase was calculated using the following Equation 1. The results of the calculation are shown in Table 1 below. Herein, the absorbance of an untreated group was used as a control group. That is, the expression of collagenase in the control group was set at 100, and the expression of collagenase in each test group was calculated relative to the control group.

$$\text{Collagenase expression (\%)} = A/B \times 100 \qquad \text{Equation 1}$$

wherein A is the absorbance of the cell group treated with each test material, and B is the absorbance of the control group.

TABLE 1

| Test material | Collagenase expression (%) |
| --- | --- |
| Control | 100 |
| Retinoic acid (positive control) | 51.3 |
| Example 1 | 81.3 |
| Example 2 | 75.7 |
| Example 3 | 52.9 |

As can be seen in Table 1 above, the collagenase expression inhibitory activity of the *Lycium chinense* extract/pine needle extract mixture of Example 3 was 2.1 times higher than those of the *Lycium chinense* extract of Example 1 and the pine needle extract of Example 2. This suggests that the use of the mixture of the *Lycium chinense* extract and the pine needle extract effectively inhibits collagenase expression compared to the use of the *Lycium chinense* extract or the pine needle extract alone.

TEST EXAMPLE 2

Effects on Retinoic Acid Receptor α/γ (RAR-α/γ) Transcriptional Activities

Using the *Lycium chinense* extract obtained in Example 1, the pine needle extract obtained in Example 2, and the *Lycium chinense* extract/pine needle extract mixture (Example 3) obtained by mixing the extract of Example 1 with the extract of Example 2, their effects on retinoic acid receptor α/γ (RAR-α/γ) transcriptional activities were measured in the following manner. As a positive control, retinoic acid known to activate retinoic acid receptor was used.

First, monkey kidney epithelial CV-1 cells were seeded into a 24-well plate at a concentration of $4 \times 10^4$ cells/well and cultured for 12-16 hours. Before transfection, the plate was washed with phosphate buffered saline (PBS), and then the medium was cultured. Meanwhile, a reporter plasmid, a receptor plasmid, a β-galactosidase expression vector and the carrier DNA pBluscript (pBS) were combined with each other to a total weight of 0.5 μg, and then added to each well containing the CV-1 cells. Then, the cells were treated with each of 100 μg/ml of the extract of Example 1, 100 μg/ml of the extract of Example 2, the mixed extract (Example 3) obtained by mixing 100 μg/ml of the extract of Example 1 with 100 μg/ml of the extract of Example 2, and 1 μM of retinoic acid, for 20 hours, and 0.25 M Tris-HCl (pH 8.0) was added thereto to prepare cell lysates. Then, each of the cell lysates was transferred to a cell culture plate (Costar) for a 96-well luminometer, and luciferase activity for each cell lysate was measured using Luciferase Assay System™ kit (Promega Corporation) according to the manufacturer's instruction.

In order to measure β-galactosidase activity, 20 μl of each of the cell lysates was transferred to a 96-well analysis plate (Falcon, Cat. No. 353911), and 100 μl of ONPG (onitrophenyl β-galacti-pyranoside) solution was added to each well, after which the plate was allowed to stand in an incubator at 37° C. for 2 hours.

Next, 50 μl of 1 M sodium carbonate ($Na_2CO_3$) solution was added to each well, and the absorbance of each well at 415 nm was measured. The efficiency of transformation in each cell lysate was corrected with the β-galactosidase activity measured as described above, and the relative activity of luciferase to the β-galactosidase activity was calculated and compared between Examples. The results are shown in Table 2 below.

TABLE 2

| Test material | Relative activity (%) of luciferase (RAR-α) | Relative activity (%) of luciferase (RAR-γ) |
|---|---|---|
| Control | 100 | 100 |
| Retinoic acid (positive control) | 343 | 385 |
| Example 1 | 187 | 195 |
| Example 2 | 209 | 179 |
| Example 3 | 357 | 315 |

As can be seen in Table 2 above, the *Lycium chinense* extract/pine needle extract mixture of Example 3 showed retinoic acid receptor α/γ (RAR-α/γ) transcriptional activities that are 2.6 times and 2.45 times higher than those of each of the *Lycium chinense* extract of Example 1 and the pine needle extract of Example 2.

The composition according to the present invention can be prepared in the following formulation examples, but is not limited thereto.

FORMULATION EXAMPLE 1

Milk Lotion

According to the composition shown in Table 3 below, milk lotion can be prepared by a conventional method.

TABLE 3

| Components | Content (wt %) |
|---|---|
| Glycerin | 8.0 |
| Butylene glycol | 4.0 |
| Hyaluronic acid extract | 5.0 |
| Beta-glucan | 7.0 |
| Carbomer | 0.1 |
| Mixture of *Lycium chinense* extract and pine needle extract | 1.0 |
| Caprylic/capric triglyceride | 8.0 |

TABLE 3-continued

| Components | Content (wt %) |
|---|---|
| Squalane | 5.0 |
| Cetearyl glucoside | 1.5 |
| Sorbitan stearate | 0.4 |
| Cetearyl alcohol | 1.0 |
| Preservative | q.s. |
| Fragrance | q.s. |
| Pigment | q.s. |
| Triethanoamine | 0.1 |
| Purified water | Balance |

FORMULATION EXAMPLE 2

Nourishing Lotion

According to the composition shown in Table 4 below, nourishing lotion can be prepared by a conventional method.

TABLE 4

| Components | Content (wt %) |
|---|---|
| Purified water | Balance |
| Glycerin | 3.0 |
| Butylene glycol | 3.0 |
| Liquid paraffin | 5.0 |
| Beta-glucan | 7.0 |
| Carbomer | 0.1 |
| Mixture of *Lycium chinense* extract and pine needle extract | 1.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.5 |
| Preservative | q.s. |
| Fragrance | q.s. |
| Pigment | q.s. |
| Triethanolamine | 0.1 |

FORMULATION EXAMPLE 3

Nourishing Cream

According to the composition shown in Table 5 below, nourishing cream can be prepared by a conventional method.

TABLE 5

| Components | Content (wt %) |
|---|---|
| Glycerin | 3.0 |
| Butylene glycol | 3.0 |
| Liquid paraffin | 7.0 |
| Beta-glucan | 7.0 |
| Carbomer | 0.1 |
| Mixture of *Lycium chinense* extract and pine needle extract | 1.0 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Preservative | q.s. |
| Fragrance | q.s. |
| Pigment | q.s. |
| Triethanolamine | 0.1 |
| Purified water | Balance |

FORMULATION EXAMPLE 4

Massage Cream

According to the composition shown in Table 6 below, massage cream can be prepared by a conventional method.

TABLE 6

| Components | Content (wt %) |
| --- | --- |
| Glycerin | 8.0 |
| Butylene glycol | 4.0 |
| Liquid paraffin | 45.0 |
| Beta-glucan | 7.0 |
| Carbomer | 0.1 |
| Mixture of *Lycium chinense* extract and pine needle extract | 1.0 |
| Caprylic/capric triglyceride | 3.0 |
| Beeswax | 4.0 |
| Cetearyl glucoside | 1.5 |
| Sorbitan sesquioleate | 0.9 |
| Vaseline | 3.0 |
| Preservative | q.s. |
| Fragrance | q.s. |
| Pigment | q.s. |
| Paraffin | 1.5 |
| Purified water | Balance |

FORMULATION EXAMPLE 5

Facial Pack

According to the composition shown in Table 7 below, a facial pack formulation can be prepared by a conventional method.

TABLE 7

| Components | Content (wt %) |
| --- | --- |
| Glycerin | 4.0 |
| Polyvinyl alcohol | 15.0 |
| Hyaluronic acid extract | 5.0 |
| Beta-glucan | 7.0 |
| Allantoin | 0.1 |
| Mixture of *Lycium chinense* extract and pine needle extract | 1.0 |
| Nonyl phenylether | 0.4 |
| Polysorbate 60 | 1.2 |
| Preservative | q.s. |
| Fragrance | q.s. |
| Pigment | q.s. |
| Ethanol | 6.0 |
| Purified water | Balance. |

FORMULATION EXAMPLE 6

Ointment

According to the composition shown in Table 8 below, an ointment can be prepared by a conventional method.

TABLE 8

| Components | Content (wt %) |
| --- | --- |
| Glycerin | 8.0 |
| Butylene glycol | 4.0 |
| Liquid paraffin | 15.0 |
| Beta-glucan | 7.0 |
| Carbomer | 0.1 |

TABLE 8-continued

| Components | Content (wt %) |
| --- | --- |
| Mixture of *Lycium chinense* extract and pine needle extract | 1.0 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Preservative | q.s. |
| Fragrance | q.s. |
| Pigment | q.s. |
| Beeswax | 4.0 |
| Purified water | Balance |

INDUSTRIAL APPLICABILITY

The composition according to the present invention contains a mixture of *Lycium chinense* fruit extract and pine needle extract, which activates retinoic acid receptor and inhibits the expression of collagenase to thereby exhibit wrinkle-reducing effects and anti-aging effects. In addition, the composition containing the mixture of the extracts has less side effects and is safe, and thus can be used in various applications, including cosmetic or drug products.

The invention claimed is:

1. A method of inhibiting the appearance of aging of the skin of a subject in need thereof, comprising applying an effective amount of a cosmetic composition containing a mixture of a *Lycium chinense* fruit extract and a pine needle extract to the skin of the subject,
    wherein the *Lycium chinense* fruit extract is obtained by extracting *Lycium chinense* fruit with aqueous ethanol to produce a mixture; filtering the mixture; and re-extracting the filtered mixture with ethyl acetate; and
    wherein the pine needle extract is obtained by extracting pine needles with aqueous ethanol to produce a mixture; filtering the mixture; and re-extracting the filtered mixture with ethyl acetate.

2. The method of claim 1, wherein the content of the *Lycium chinense* extract is 40-60 wt% based on the total weight of the mixture.

3. The method of claim 1, wherein the content of the pine needle extract is 40-60 wt% based on the total weight of the mixture.

4. The method of claim 1, wherein the weight ratio of *Lycium chinense* extract to pine needle extract in the mixture is 1:1.

5. The method of claim 1, wherein said applying reduces wrinkles of the skin.

6. The method of claim 1, wherein the composition is in a formulation selected from the group consisting of skin lotion, milk lotion, massage cream, nourishing cream, moisturizing cream, hand cream, foundation, essence, nourishing essence, cream, soap, cleansing foam, cleansing lotion, cleansing cream, body lotion, body cream, and facial mask formulations.

7. A method of inhibiting the appearance of aging of the skin of a subject in need thereof, comprising applying an effective amount of a pharmaceutical composition containing a mixture of a *Lycium chinense* fruit extract and a pine needle extract to the skin of the subject,
    wherein the *Lycium chinense* fruit extract is obtained by extracting *Lycium chinense* fruit with aqueous ethanol to produce a mixture; filtering the mixture; and re-extracting the filtered mixture with ethyl acetate; and wherein the pine needle extract is obtained by extracting pine needles with aqueous ethanol to produce a mixture; filtering the mixture; and re-extracting the filtered mixture with ethyl acetate.

8. The method of claim 7, wherein the weight ratio of *Lycium chinense* extract to pine needle extract in the mixture is 1:1.

9. The method of claim 7, wherein said applying reduces wrinkles of the skin.

10. The method of claim 7, wherein the composition is in a formulation selected from the group consisting of suspension, ointment, lotion, and spray formulations.

\* \* \* \* \*